United States Patent
Nagai

(10) Patent No.: US 9,702,831 B2
(45) Date of Patent: Jul. 11, 2017

(54) OBJECT INFORMATION OBTAINING APPARATUS, PROGRAM, AND IMAGING SYSTEM

(71) Applicant: CANON KABUSHIKI KAISHA, Tokyo (JP)

(72) Inventor: Kentaro Nagai, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 212 days.

(21) Appl. No.: 14/651,187

(22) PCT Filed: Dec. 12, 2013

(86) PCT No.: PCT/JP2013/084168
§ 371 (c)(1),
(2) Date: Jun. 10, 2015

(87) PCT Pub. No.: WO2014/092206
PCT Pub. Date: Jun. 19, 2014

(65) Prior Publication Data
US 2015/0308967 A1     Oct. 29, 2015

(30) Foreign Application Priority Data

Dec. 13, 2012 (JP) ................. 2012-272672

(51) Int. Cl.
*G03H 3/00*     (2006.01)
*G01N 23/04*     (2006.01)
(Continued)

(52) U.S. Cl.
CPC ............. *G01N 23/04* (2013.01); *G01N 23/20* (2013.01); *G21K 1/06* (2013.01); *H01J 37/252* (2013.01); *H01J 2237/221* (2013.01)

(58) Field of Classification Search
None
See application file for complete search history.

(56) References Cited

U.S. PATENT DOCUMENTS 5,969,855 A * 10/1999 Ishiwata ............. G02B 21/367
359/370
9,060,736 B2 * 6/2015 Nakamura ............. G01N 23/04
(Continued)

FOREIGN PATENT DOCUMENTS

CN     102451012 A  *  5/2012  ........... A61B 6/4233
CN     102551751 A  *  7/2012  ........... A61B 6/4291
(Continued)

OTHER PUBLICATIONS

Fang, et al., "Latest Development of First-Order Commensurate CT Reconstruction Algorithm", CT Theory & Application Research, vol. 17, No. 4, pp. 23-31, Dec. 2008.

(Continued)

*Primary Examiner* — Andrew Smyth
(74) *Attorney, Agent, or Firm* — Canon USA, Inc. I.P. Division

(57) ABSTRACT

The present invention relates to an object information obtaining apparatus that obtains information about a phase image of an object using information about an interference pattern produced by a shearing interferometer, the interference pattern being formed by an electromagnetic wave or electron beam passed through or reflected by the object. The apparatus includes a first obtaining unit configured to obtain information about a differential phase image of the object using the information about the interference pattern, a second obtaining unit configured to obtain information about contrast in each region of the interference pattern, a third obtaining unit configured to weight the information about the differential phase image using the information about the contrast to obtain information about a weighted differential phase image, and a fourth obtaining unit configured to integrate the information about the weighted differential
(Continued)

phase image to obtain the information about the phase image of the object.

17 Claims, 8 Drawing Sheets

(51) Int. Cl.
  *G21K 1/06* (2006.01)
  *G01N 23/20* (2006.01)
  *H01J 37/252* (2006.01)

(56) References Cited

U.S. PATENT DOCUMENTS

| | | | | |
|---|---|---|---|---|
| 9,510,799 | B2* | 12/2016 | Makifuchi | A61B 6/4291 |
| 2011/0235775 | A1* | 9/2011 | Tada | A61B 6/00 |
| | | | | 378/36 |
| 2012/0099702 | A1* | 4/2012 | Engel | A61B 6/00 |
| | | | | 378/62 |
| 2012/0183123 | A1* | 7/2012 | Tada | G01N 23/046 |
| | | | | 378/62 |

FOREIGN PATENT DOCUMENTS

| | | | | |
|---|---|---|---|---|
| EP | 2865336 A1 * | 4/2015 | | A61B 6/4233 |
| JP | 2009-525084 | 7/2009 | | |
| JP | 4445397 B2 * | 4/2010 | | A61B 6/06 |
| JP | WO 2010050483 A1 * | 5/2010 | | G01N 23/04 |
| JP | 2011-224329 A | 11/2011 | | |
| JP | 2011224329 A * | 11/2011 | | G01N 23/04 |
| JP | 2012-507690 A | 3/2012 | | |
| JP | 5193204 B2 * | 5/2013 | | D21H 23/50 |
| WO | 2010/050483 A1 | 5/2010 | | |

OTHER PUBLICATIONS

Thuring, et al., "Non-linear regularized phase retrieval for unidirectional X-ray differential phase contrast radiography", Optics Express, Dec. 5, 2011, pp. 25545-25558, vol. 19, No. 25.

David, et al., "Differential x-ray phase contrast imaging using a shearing interferometer", Applied Physics Letters, Oct. 21, 2002, pp. 3287-3289, vol. 81, No. 17.

* cited by examiner

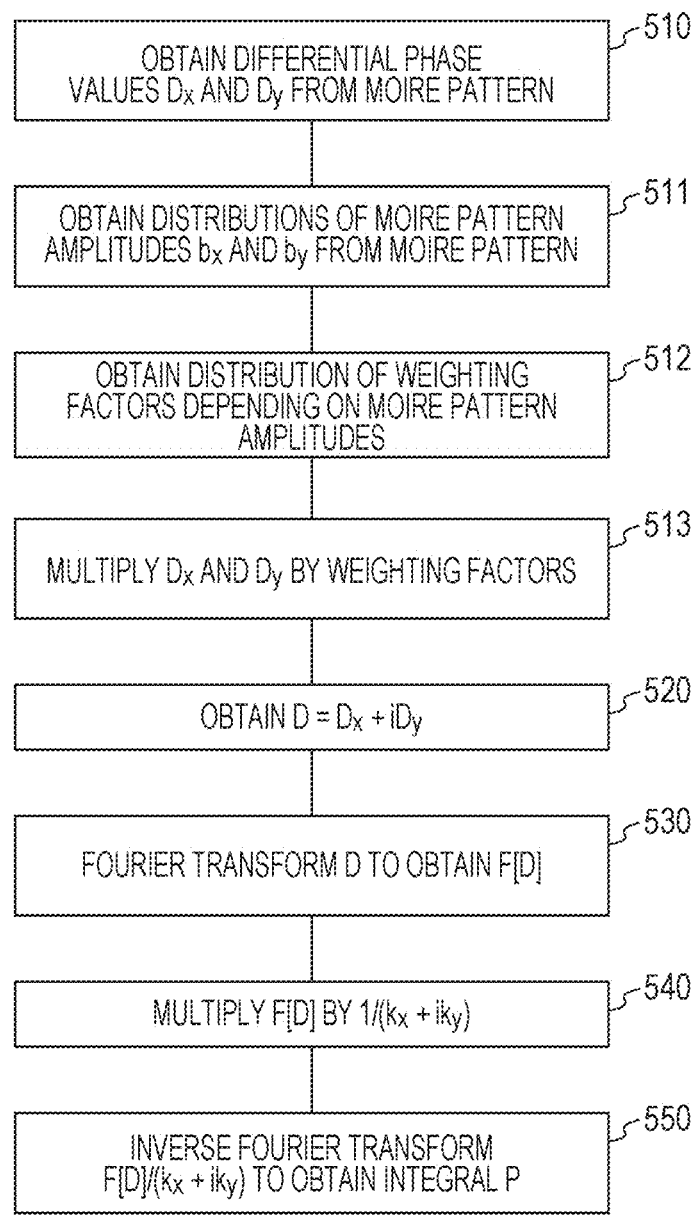

OBJECT INFORMATION OBTAINING APPARATUS, PROGRAM, AND IMAGING SYSTEM

TECHNICAL FIELD

The present invention relates to an object information obtaining apparatus that obtains information about a phase image from an interference pattern produced by a shearing interferometer, a program, and an imaging system.

BACKGROUND ART

A shearing interferometer is used to observe a change in phase of incident light caused by an object using displacement of interference fringes. The shearing interferometer is configured to split coherent light, such as a light beam, emitted from a light source, allow a wavefront of one light component to have a distortion caused by an object, and slightly displace the other light component to form interference fringes. Instead of light, an electromagnetic wave other than light, for example, X-rays, or an electron beam can be used.

Shearing interferometers using Talbot effect have been known. In particular, Talbot interferometry using X-rays (X-ray Talbot interferometry) has recently attracted attention.

An X-ray Talbot interferometer will now be described in brief. When X-rays from an X-ray source pass through an object, a phase of the X-rays is shifted. The X-rays passed through the object are diffracted by a diffraction grating, thus forming a first interference pattern, called a self-image, at a position at a predetermined distance from the diffraction grating. A phase shift of the X-rays caused by the object can be obtained based on a distortion in the first interference pattern caused by the object. Depending on the resolution of a detector used, however, it may be difficult to directly detect the first interference pattern because the period of fringe pattern is too small to detect the standard detector. To overcome the above problem, there has been proposed a method of forming a second interference pattern, or moire pattern having a period of approximately several hundreds of micrometers by disposing an absorption grating at the position of a first interference pattern formed, the absorption grating having almost the same period as that of the first interference pattern. A distortion in the first interference pattern can be detected indirectly by detecting the moire pattern having the period which is sufficiently large to be detected by the detector.

There are some methods (phase demodulation methods) of obtaining information (object differential phase information) about a phase shift caused by an object from a second interference pattern. An example of the methods is the Fourier transform method (refer to PTL 1). According to this method, a second interference pattern is Fourier transformed and object phase information is obtained from information associated with a region surrounding a spectrum corresponding to carrier frequencies obtained by Fourier transforming the second interference pattern.

Another typical phase demodulation method is the phase shift method (refer to PTL 2). According to this method, typically, the position of an absorption grating relative to an interference pattern is shifted by a distance corresponding to a fraction of the period of the absorption grating to shift a phase, thus changing a second interference pattern. The second interference patterns are detected in each position of the absorption grating. Object phase information is obtained based on changes as detection results. In addition, a method as a combination of the Fourier transform method and the phase shift method and any other methods may be used. In the phase shift method, the period of a second interference pattern may be greater than or equal to the size of a detector or may be infinite. Second interference patterns formed using the above-described methods are also included in moire patterns in this specification.

Since the Talbot interferometer is the shearing interferometer, primary information obtained by phase demodulation using a second interference pattern is a derivative of a phase shift of X-rays caused by an object (or information about a differential phase image of the object). Accordingly, to obtain phase information about the object, the information about the differential phase image has to be integrated. Although there are some integration methods, the information about the differential phase image can be simply integrated by sequentially adding up the information in accordance with a differentiation method.

CITATION LIST

Patent Literature

[PTL 1]
International Publication No. WO 10/050483
[PTL 2]
Japanese Patent No. 4445397

SUMMARY OF INVENTION

The present invention provides an object information obtaining apparatus that obtains information about a phase image of an object using information about an interference pattern produced by a shearing interferometer, the interference pattern being formed by an electromagnetic wave or electron beam passed through or reflected by the object. The apparatus includes a first obtaining unit configured to obtain information about a differential phase image of the object using the information about the interference pattern, a second obtaining unit configured to obtain information about contrast in each region of the interference pattern, a third obtaining unit configured to weight the information about the differential phase image using the information about the contrast to obtain information about a weighted differential phase image, and a fourth obtaining unit configured to integrate the information about the weighted differential phase image to obtain the information about the phase image of the object.

Further features of the present invention will become apparent from the following description of exemplary embodiments with reference to the attached drawings.

BRIEF DESCRIPTION OF DRAWINGS

FIG. 4 is a flowchart of an arithmetic process performed by the object information obtaining apparatus in Example 1.

DESCRIPTION OF EMBODIMENTS

The inventor of the present invention has revealed the following: If a second interference pattern includes a low contrast region, it may be difficult to measure a shift of the interference pattern in the region, depending on contrast. As described above, information about a phase image of an object is obtained based on a shift of the second interference pattern caused by the object. As regards information about a differential phase image, the information may be missing or the influence of noise may be increased in a region, included in the differential phase image, corresponding to the low contrast region. If the information about the differential phase image including a region where the information is missing and a region where the influence of noise is large is integrated, the influences of the regions may affect the other region such that the accuracy of the obtained information about the phase image may be reduced.

Embodiments, which will be described below, provide an object information obtaining apparatus capable of, when obtaining information about a phase image from information about a differential phase image including a region where the information about the differential phase image is missing and a region where the influence of noise is large, reducing the influences of the regions, a program, and an imaging system.

Figure 1:
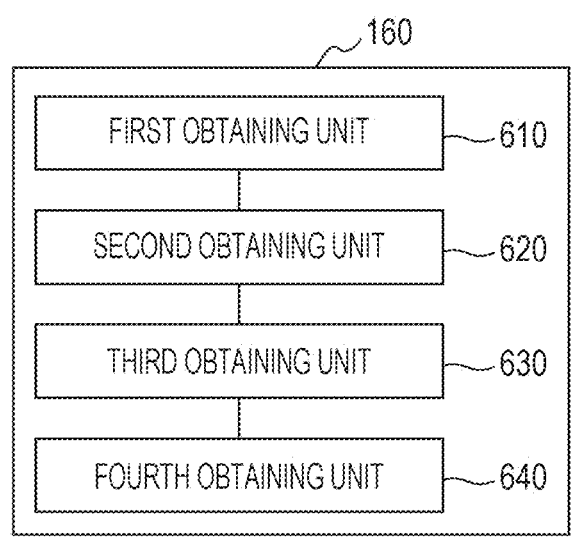
FIG. 1 is a functional block diagram of an object information obtaining apparatus according to an embodiment.

An embodiment provides an object information obtaining apparatus that obtains information about a phase image of an object using information about an interference pattern produced by a shearing interferometer. FIG. 1 is a functional block diagram of the object information obtaining apparatus according to the present embodiment. The object information obtaining apparatus, indicated at 160, includes a first obtaining unit 610, a second obtaining unit 620, a third obtaining unit 630, and a fourth obtaining unit 640. The first obtaining unit 610 is configured to obtain information (hereinafter, also referred to as "differential phase image information") about a differential phase image of an object using information about an interference pattern. The second obtaining unit 620 is configured to obtain information (hereinafter, also referred to as "contrast information") about contrast in each region of the interference pattern. The third obtaining unit 630 is configured to weight the differential phase image information using the contrast information obtained by the second obtaining unit 620 to obtain information (hereinafter, also referred to as "weighted differential phase image information") about a weighted differential phase image. The fourth obtaining unit 640 is configured to integrate the weighted differential phase image information obtained by the third obtaining unit 630 to obtain information about a phase image of the object. The interference pattern is formed by an electromagnetic wave or electron beam passed through the object.

Typically, if information about a differential phase image of an object is obtained using an interference pattern including a low contrast region, the information may be missing or noise may increase in a region, included in the differential phase image, corresponding to the low contrast region. Accordingly, the accuracy of information associated with the region is lower than that associated with the other region. When the information about the differential phase image including the region with low accuracy is integrated, the information associated with the low accuracy region affects information associated with the other region, leading to reduced accuracy of the information associated with the other region. According to the present embodiment, as described above, differential phase image information is weighted using information about contrast of an interference pattern, and the weighted differential phase image information is integrated. Thus, if information about a differential phase image including a region with low accuracy is integrated, the influence of information associated with the region on information associated with the other region can be reduced.

An exemplary embodiment of the present invention will be described below with reference to the attached drawings. In the figures, the same components are designated by the same reference numerals and redundant description is avoided. Although an X-ray Talbot interferometer is used as a shearing interferometer in the present embodiment, any of general shearing interferometers for causing interference to obtain a differential phase can be used. Furthermore, an electromagnetic wave other than X-rays or an electron beam can be used instead of X-rays.

Figure 2:
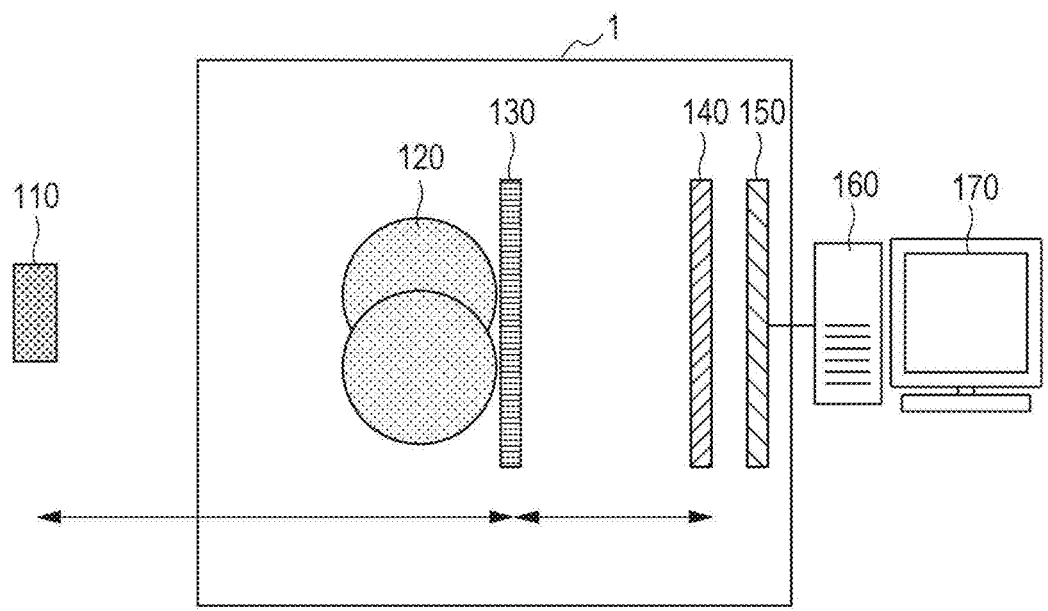
FIG. 2 is a schematic diagram of an X-ray imaging system according to an embodiment.

FIG. 2 is a schematic diagram illustrating the configuration of an imaging system according to the present embodiment. The imaging system includes an X-ray source 110, a Talbot interferometer 1, the object information obtaining apparatus 160 configured to obtain information about a phase image of an object using information about an interference pattern produced by the Talbot interferometer 1, and an image display apparatus 170 configured to display an image based on a result of arithmetic processing by the object information obtaining apparatus 160. The components will be described below.

The X-ray source 110 is configured to emit X-rays having spatial coherence sufficient to allow an interference pattern to be formed due to interference caused by a shearing interferometer. In the use of the Talbot interferometer 1 as a shearing interferometer, a diffraction grating 130 of the Talbot interferometer 1 may be irradiated with X-rays having spatial coherence sufficient to allow an interference pattern, called a self-image, to be formed by diffraction through the diffraction grating 130.

The Talbot interferometer 1 includes the diffraction grating 130 configured to diffract X-rays from the X-ray source 110, an absorption grating 140 configured to partially block a self-image, and a detector 150 configured to detect X-rays from the absorption grating 140.

The diffraction grating 130 is configured to diffract X-rays from the X-ray source 110 to form a self-image at a position at a predetermined distance from the diffraction grating 130 such that the self-image includes bright parts and dark parts arranged in an arrangement direction. In the specification, the intensity of X-rays (or any other electromagnetic wave or an electron beam) in the bright part is high and that in the dark part is low. As regards the kind of diffraction grating, a phase diffraction grating (phase grating) configured to periodically modulate the phase may be used or an amplitude diffraction grating configured to periodically modulate the amplitude may be used. Using the phase grating is more advantageous because of little loss of the amount of X-rays (or the amount of any other electromagnetic wave or electron beam). Furthermore, a diffraction grating (one-dimensional diffraction grating) having periodicity in one direction may be used. Alternatively, a diffraction grating (two-dimensional diffraction grating) having periodicity in two directions may be used.

The absorption grating 140 is configured to partially block the self-image to form a moire pattern.

A typical self-image formed by the diffraction grating 130 has a period of approximately several to several tens of micrometers. The period can be increased to be greater than or equal to several tens of micrometers or infinite by forming a moire pattern through the absorption grating 140 in which blocking parts and transmitting parts are arranged at the same period as that of the self-image or a period slightly different from that of the self-image. Consequently, the self-image can be detected (resolved) even in the use of the detector 150 having a resolution of approximately several tens of micrometers square. The self-image and the moire pattern are kinds of interference pattern. The absorption grating 140 may be omitted if the detector 150 can directly detect a self image, for example, when the detector 150 has a sufficiently high resolution or when the enlargement ratio of the self image is high because of a long distance between the diffraction grating 130 and the detector 150. The absorption grating 140 may be an absorption grating (absorption grating) configured to absorb X-rays (or any other electromagnetic wave or an electron beam) or an absorption grating configured to reflect X-rays (or any other electromagnetic wave or an electron beam).

The detector 150, which is configured to detect X-rays from the absorption grating 140, can obtain information about a two-dimensional X-ray intensity distribution depending on the intensities of applied X-rays. Instead of the information about the two-dimensional X-ray intensity distribution, information about a one-dimensional X-ray intensity distribution may be obtained using a line sensor.

An object 120 is placed between the diffraction grating 130 and the X-ray source 110. Since X-rays typically have high penetrability, X-rays pass through the object 120. At this time, the phase of X-rays shifts depending on the composition and density of the object 120. The phase shift affects the shape of a self-image. Accordingly, the shape of a moire pattern formed by the self-image and the absorption grating 140 also changes. When the detector 150 detects the moire pattern, information about an image (also called an "object phase image" or simply called a "phase image") of the phase shift of X-rays caused by the object 120 can be obtained from information about the detected moire pattern. Although the object 120 is placed between the X-ray source 110 and the diffraction grating 130 in FIG. 2, the object 120 may be placed between the diffraction grating 130 and the absorption grating 140.

The outline of the X-ray Talbot interferometer 1 has been described above.

The object information obtaining apparatus 160 is connected to the detector 150 via a cable. The information about the moire pattern (hereinafter, "moire pattern information") detected by the detector 150 is transmitted to the object information obtaining apparatus 160 and is then subjected to an arithmetic process, which will be described later, to obtain information about a phase image of the object 120. The information about the phase image is information representing the phase image and means information indicating phase values at respective coordinates. The same applies to information about a differential phase image.

Functions of the object information obtaining apparatus 160 will be described with reference to the block diagram of FIG. 1.

The first obtaining unit 610 obtains information (hereinafter, "differential phase image information") about a differential phase image of the object 120 using the more pattern information transmitted from the detector 150 (phase demodulation). Any method of obtaining the differential phase image information may be used. As methods for phase demodulation using a result of detection by an X-ray Talbot interferometer, the Fourier transform method, the phase shift method, the method as the combination of the Fourier transform method and the phase shift method, and other various methods have been known. Any of the methods may be used. The first obtaining unit 610 may obtain differential phase image information about the object 120 by receiving the information from a differential phase imaging device configured to obtain differential phase image information about an object using information about an interference pattern.

The second obtaining unit 620 obtains information (hereinafter, also referred to as "contrast information") about contrast in each region of the moire pattern. The contrast information may be information relating to contrast. For example, information relating to the amplitude of the moire pattern or information relating to the X-ray dosage of the object 120 (quantity of X-ray absorption by the object) can be used. Specific examples of the information relating to the amplitude of a moire pattern include information about the visibility of the moire pattern and information about the amplitude of the moire pattern. Specific examples of the information relating to the X-ray dosage of an object include information about the X-ray dosage and information about the absorption rate of X-rays. As the X-ray dosage increases, the intensity of X-rays detected by the detector 150 decreases. Accordingly, information about the intensity of X-rays detected can also be used as information relating to the X-ray dosage of an object. Since the third obtaining unit 630 weights the differential phase image information depending on the contrast of the moire pattern, the information about the contrast of the moire pattern is obtained in each region of an interference pattern. The regions of the interference pattern may be obtained by dividing the interference pattern detected by the detector 150 into parts. Any manner of dividing the interference pattern into regions may be used. The interference pattern may be divided such that regions have a one-to-one correspondence to pixels of the detector 150. Alternatively, the interference pattern may be divided such that each region corresponds to a plurality of pixels. As the interference pattern is divided into smaller regions, weighting by the third obtaining unit 630 can be performed more finely. In cases where a moire pattern is Fourier transformed, information about the amplitude of the moire pattern and information about the X-ray dosage can be obtained as distributions without division of the interference pattern into regions. Accordingly, these information items can also be used. In this case, each of data items representing the distribution corresponds to a region of the interference pattern.

The third obtaining unit 630 weights the differential phase image information using the contrast information obtained by the second obtaining unit 620 to obtain information (hereinafter, also referred to as "weighted differential phase image information") about a weighted differential phase image. In this case, information associated with a region corresponding to a low contrast region of the interference pattern is weighted so as to be lighter than information associated with the other region (corresponding to the other region in which contrast is higher than that in the low contrast region). In the following description, the other region will be referred to as a "high contrast region". Although the first obtaining unit 610 has obtained the differential phase image information whose values (hereinafter, also referred to as "differential phase values") are derivatives of the phase shift, differential phase values less than those obtained by the first obtaining unit 610 are obtained in the region corresponding to the low contrast region of the interference pattern by the above-described weighting. On the other hand, differential phase values greater than those obtained by the first obtaining unit 610 are obtained in the region corresponding to the high contrast region of the interference pattern. The above-described weighting may be performed such that a weighting factor for the information associated with the region corresponding to the low contrast region (second region) is smaller than that for the information associated with the region corresponding to the high contrast region (first region). As regards a method of setting the weighting factors as described above, for example, a weighting function that obtains weighting factors from the contrast information can be used. In the use of the weighting function, the weighting function may be previously stored in a storage unit or may be generated by the third obtaining unit 630. According to the weighting function, for example, a value of information about contrast in a given region of the interference pattern is compared with a threshold value and a weighting factor for the region is determined based on a result of determination as to whether the value of the contrast information associated with the region is greater than or equal to the threshold value. When the value of the contrast information associated with each of the regions of the interference pattern is greater than or equal to the threshold value, a constant weighting factor may be used for differential phase image information obtained from the interference pattern. Furthermore, the same weighting factor may be determined for information items associated with regions corresponding to regions with different values as contrast information. For example, the same weighting factor as that for information associated with a region corresponding to the high contrast region may be used for information associated with a region corresponding to an intermediate contrast region (third region). Alternatively, the same weighting factor as that for information associated with a region corresponding to the low contrast region may be used for the information associated with the region corresponding to the intermediate contrast region. The intermediate contrast region means a region in which contrast is lower than that in the high contrast region and is higher than that in the low contrast region.

The fourth obtaining unit 640 integrates the weighted differential phase image information obtained by the third obtaining unit 630 to obtain information (hereinafter, also referred to as "object phase image information") about a phase image of the object 120. Any integration method may be used. Various methods, such as a method of simple adding up from one end and a method using the Fourier transform, may be used. A method of integrating differential phase image information using the Fourier transform and a method of obtaining differential phase image information from moire pattern information using the Fourier transform are independent methods. Accordingly, differential phase image information obtained using the Fourier transform may be integrated without using the Fourier transform. Alternatively, differential phase image information obtained without using the Fourier transform may be integrated using the Fourier transform. In the following description, the former method will be referred to as "Fourier transform integration" and the latter method will be referred to as "Fourier transform phase demodulation" to discriminate between these methods.

The Fourier transform integration is known to reduce the influence of noise and accordingly obtain an integral with higher accuracy than that obtained by the method of simple adding up from one end. The Fourier transform integration, however, has a disadvantage in that this method is susceptible to random noise, such as missing information. Accordingly, the effect of weighting by the third obtaining unit 630 on the Fourier transform integration is larger than that on the method of simple adding up.

The object information obtaining apparatus 160 has only to perform arithmetic processing, which will be described later, using the moire pattern information transmitted from the detector 150. For example, the object information obtaining apparatus 160 can be implemented by a computer including an arithmetic unit including a calculator, such as a central processing unit (CPU), a main storage unit including a volatile memory, such as a random-access memory (RAM), and an auxiliary storage unit including a non-volatile memory, such as a hard disk drive (HDD). The functions of the first to fourth obtaining units 610 to 640 are implemented by loading a program stored in the auxiliary storage unit into the main storage unit and executing the program through the arithmetic unit. The above-described configuration is illustrative only and the object information obtaining apparatus 160 may have any configuration.

The image display apparatus 170 is connected to the object information obtaining apparatus 160 and is capable of displaying an image based on object phase image information obtained by the object information obtaining apparatus 160. The image display apparatus 170 may display a differential phase image of an object and other information. The image display apparatus 170 is a monitor capable of displaying an image. For example, a cathode ray tube (CRT) or a liquid crystal display (LCD) may be used.

The embodiment has been described with respect to the imaging system including the X-ray Talbot interferometer as a shearing interferometer. In a shearing interferometer using a wavefront of X-rays passed through an object in a manner similar to the X-ray Talbot interferometer, depending on object, X-rays may be absorbed by the object or the wavefront of X-rays may be affected by random scattering at a period shorter than that of a moire pattern. Accordingly, the contrast of the moire pattern tends to decrease. If phase image information is obtained using an interference pattern formed by an electromagnetic wave or electron beam reflected by an object, similarly, absorption or random scattering of the electromagnetic wave or electron beam may occur depending on object. Accordingly, the advantages of the embodiment can be obtained in this case.

COMPARATIVE EXAMPLE

Comparative Example will be described with respect to a method of integrating differential phase image information obtained using a moire pattern without weighting the information to obtain phase image information. Comparative Example uses a two-dimensional moire pattern for allowing differential phase images in two directions (X direction and Y direction) to be obtained using the single moire pattern. Since the method is the same as that in the imaging system described in the foregoing embodiment, except for an arithmetic process performed by an object information obtaining apparatus, the description thereof is omitted.

Figure 8:
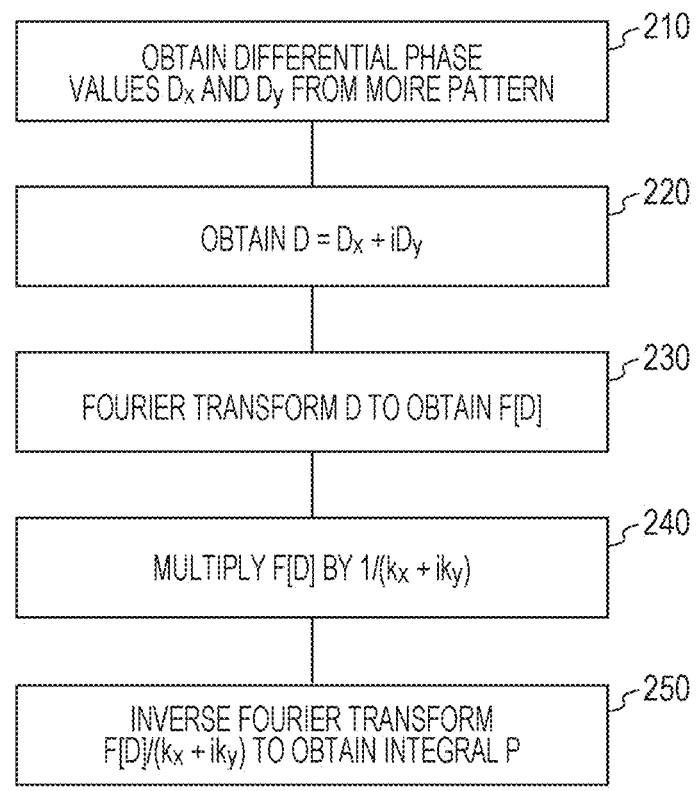
FIG. 8 is a flowchart of an arithmetic process performed by an object information obtaining apparatus according to Comparative Example.

FIG. 8 is a flowchart of the arithmetic process performed by the object information obtaining apparatus in Comparative Example.

First, information about a differential phase image in the X direction and a differential phase image in the Y direction are obtained using a moire pattern transmitted from a detector (S210). Differential phase values in the X and Y directions obtained in S210 are denoted by $D_x(x, y)$ and $D_y(x, y)$, respectively. Coordinates (x, y) denote differential phase values at this point. Comparative Example uses the Fourier transform phase demodulation as a phase demodulation method.

Then, information about a phase image is obtained using $D_x(x, y)$ and $D_y(x, y)$ obtained in S210 by the Fourier transform integration (S220 to S250). The steps of the Fourier transform integration in Comparative Example will be described below.

The Fourier transform integration uses the following function expressed as a complex number composed of $D_x(x, y)$ and $D_y(x, y)$ (S220).

$$D(x, y) = D_x(x, y) + iD_y(x, y) \quad (1)$$

where i denotes the imaginary unit. It is known that an integral P including $D_x$ and $D_y$ as differential components is obtained based on the value D by the following calculation (S230 to S250).

[Math. 1]

$$P = F^{-1}\left[\frac{F[D(x, y)]}{k_x + ik_y}\right] \quad (2)$$

In Equation (2), F[ . . . ] is the operator of the Fourier transform on the function in brackets, $F^{-1}$[ . . . ] is the operator of the inverse Fourier transform on the function in brackets, and $k_x$ and $k_y$ denote wave numbers in the Fourier space.

To perform this calculation, according to Comparative Example, D(x, y) is Fourier transformed to obtain F[D(x, y)] (S230).

Subsequently, F[D(x, y)] is multiplied by $1/(k_x+ik_y)$ to obtain $F[D(x, y)]/(k_x+ik_y)$ (S240). Then, $F[D(x, y)]/(k_x+ik_y)$ is inverse Fourier transformed to obtain the integral P (S250). The obtained P represents the distribution of phase shifts, namely, phase image information. A phase image can be obtained by mapping this information.

Figure 3:
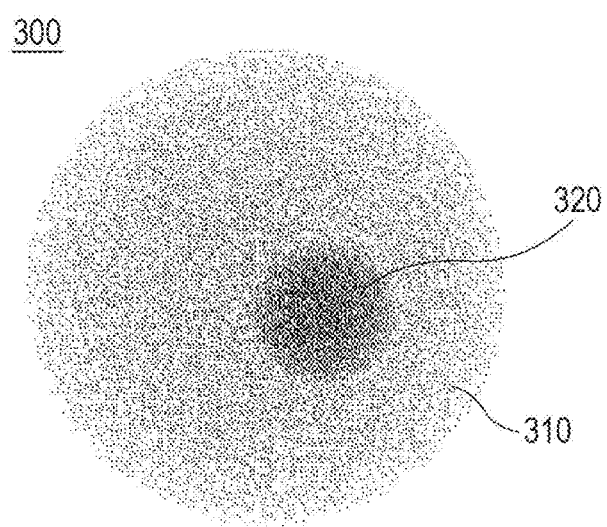
FIG. 3 is a schematic diagram of an object in Example 1, Example 2, and Comparative Example.

A simulation was performed such that an object illustrated in FIG. 3 was imaged and information about a phase image of the object was obtained by the above-described arithmetic process. An object 300 illustrated in FIG. 3 is a spherical substance 310 which has high transparency and has therein a spherical substance 320 which has low transparency and a complex structure. When an object having a low transparency region or a region having a complex structure, like the substance 320 in the object 300, is imaged, the region may cause a decrease in contrast of an interference pattern. The term "complex structure" means a structure having a random pattern less than or equal to the period of the diffraction grating. If an object has a region with a complex structure, the structure randomly reflects coherent X-rays (or another electromagnetic wave or an electron beam) entered the structure, thus reducing contrast of an interference pattern.

Figure 9A:
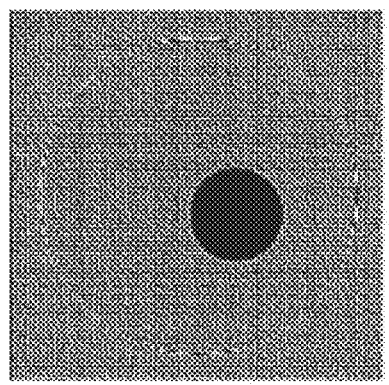
FIG. 9A illustrates a moire pattern used for simulation in Comparative Example.
Figure 9B:
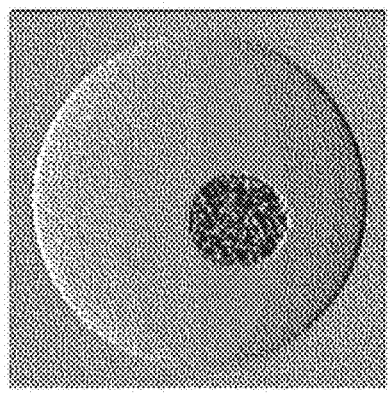
FIG. 9B illustrates a differential phase image simulated in Comparative Example.
Figure 9C:
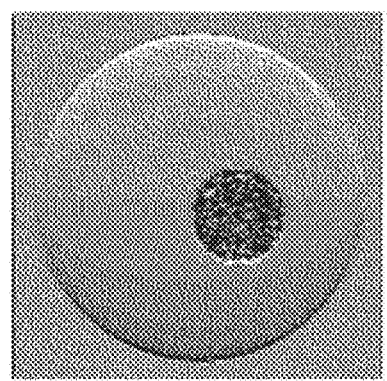
FIG. 9C illustrates another differential phase image simulated in Comparative Example.
Figure 9D:
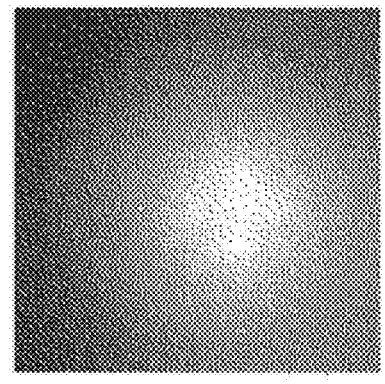
FIG. 9D illustrates a phase image simulated in Comparative Example.

FIG. 9A illustrates a moire pattern used in the simulation for obtaining a phase image of the object 300. FIGS. 9B and 9C illustrate images (differential phase images) based on the differential phase image information obtained in S210. FIG. 9D illustrates an image (phase image) based on the integral obtained in S250.

FIG. 9A demonstrates that the contrast in a region, corresponding to the substance 320 having low transparency, of the moire pattern is lower than that in the other region and the moire pattern in the low contrast region cannot be observed. FIGS. 9B and 9C illustrate the differential phase images obtained using this moire pattern by processing in S210. In FIGS. 9B and 9C, the lateral direction is the X direction and the longitudinal direction is the Y direction. FIG. 9B illustrates the differential phase image in the Y direction and FIG. 9C illustrates the differential phase image in the X direction. As can be seen from these differential phase images, a random differential phase pattern is generated in a region corresponding to the low contrast region where the contrast of the moire pattern was reduced by the influence of the substance 320. These images (information) do not reflect an actual shape or state of the object. FIG. 9D illustrates the phase image obtained using the differential phase image information illustrated in FIGS. 9B and 9C by processing in S220 to S250. The region with the random pattern, generated by the influence of the substance 320, affected the surrounding region (i.e., a region corresponding to the substance 310, or the region corresponding to the high contrast region of the moire pattern) during integration, thus reducing the accuracy of obtained phase image values in the surrounding region. As described above, when information about a phase image is obtained using a moire pattern including a low contrast region, the accuracy of the phase image is reduced not only in a region corresponding to the low contrast region but also in the other region corresponding to the surrounding region.

EXAMPLE 1

Example 1 of the present invention will be described below. In Example 1, a simulation was performed such that information about a phase image was obtained using the same moire pattern as that (see FIG. 9A) used in Comparative Example. Example 1 agrees with Comparative Example in that differential phase image information was obtained from moire pattern information but differs from Comparative Example in that the obtained differential phase image information was weighted and the weighted differential phase image information was integrated.

FIG. 4 is a flowchart of an arithmetic process performed by the object information obtaining apparatus 160 in Example 1. In Example 1, the first obtaining unit 610 obtains information ($D_x(x, y)$ and $D_y(x, y)$) about differential phase images from the moire pattern (S510). The second obtaining unit 620 obtains distributions ($b_x(x, y)$ and $b_y(x, y)$) of moire pattern amplitudes for each region of the moire pattern (S511). The third obtaining unit 630 obtains the distribution (weighting map information) of weighting factors depending on the moire pattern amplitudes (S512) and multiplies the differential phase image information by the distribution of weighting factors (S513). Thus, information about weighted differential phase images is obtained. The fourth obtaining unit 640 integrates the weighted differential phase image information using the Fourier transform (S520 to S550), thus obtaining information about a phase image.

Although any method of obtaining the distributions of moire pattern amplitudes performed by the second obtaining unit 620 maybe used, the distributions of moire pattern amplitudes can be obtained simultaneously when the differential phase image information is obtained. For example, according to the Fourier transform phase demodulation, a moire pattern is Fourier transformed, a carrier frequency peak derived from an obtained Fourier space is moved to the origin, and the inverse Fourier transform is then performed to obtain phases (arguments), thus obtaining differential phase image information (refer to PTL 1 for more information). The distributions of moire pattern amplitudes in the X and Y directions can be obtained by obtaining absolute values instead of arguments. In Example 1, the distributions of moire pattern amplitudes are obtained using such a method. Distributions of moire pattern amplitudes may be obtained independently of obtaining the differential phase image information.

The third obtaining unit 630 normalizes the distributions of moire pattern amplitudes obtained by the second obtaining unit 620, substitutes the normalized values into a weighting function m, thus obtaining information about a weighting map. The weighting map includes indicators each having, for example, a value greater than or equal to 0 and less than or equal to 1 to indicate the reliability of a moire pattern at a corresponding point.

Let $b_x$ and $b_y$ denote values obtained by normalizing the moire pattern amplitudes in the X and Y directions, obtained by the above-described method, in the range of 0 to 1. The weighting function (m) to determine a weighting factor is defined as follows.

[Math. 2]

$$m = \begin{cases} 1 & (\text{provided } (b_x \times b_y) \geq T_h) \\ (b_x \times b_y)/T_h & (\text{provided } (b_x \times b_y) < T_h) \end{cases} \quad (3)$$

In Equation (3), $T_h$ denotes a given threshold. The threshold can be determined depending on various factors, e.g., an object and conditions of the apparatus. The threshold value may be constant at all times, may be changed for each imaging, or may be changed at desired time. Alternatively, the threshold value may be automatically obtained depending on various conditions by the apparatus or may be set by a user. In Example 1, $T_h$=0.8. This value is stored in the storage unit of the object information obtaining apparatus 160.

Figure 5A:
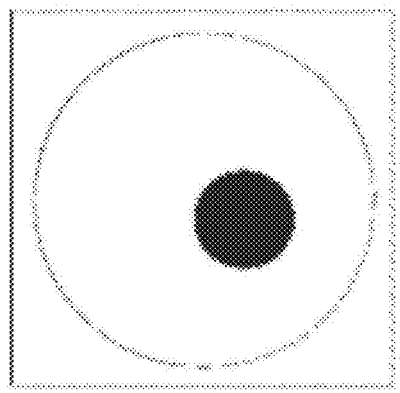
FIG. 5A illustrates a weighting map in Example 1.

FIG. 5A illustrates the weighting map obtained by substituting the values $b_x$ and $b_y$ at respective coordinates into Equation (3). As the color of a region in FIG. 5A is brighter, a weighting factor for the region is closer to 1. As the color of a region is darker, a weighting factor for the region is closer to 0. FIG. 5A demonstrates that a weighting factor for the region corresponding to the low contrast region of the moire pattern is smaller than a weighting factor for the other region.

Figure 5B:
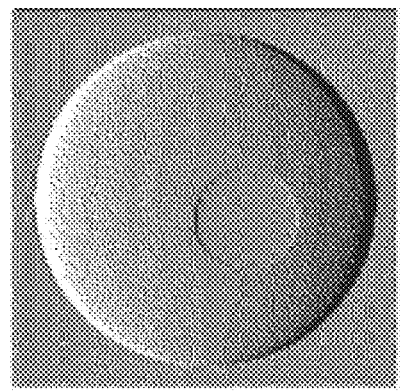
FIG. 5B illustrates a differential phase image simulated using the weighting map in Example 1.
Figure 5C:
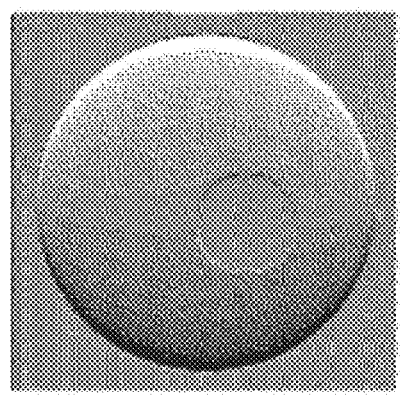
FIG. 5C illustrates another differential phase image simulated using the weighting map in Example 1.

In addition, the third obtaining unit 630 multiplies the differential phase image information, obtained by the first obtaining unit 610, by the weighting map information (S513). As regards the differential phase image information obtained by the first obtaining unit 610, the same information as that obtained in Comparative Example described above was used. The information illustrated in FIGS. 9B and 9C was used as differential phase image information obtained by the first obtaining unit 610 and multiplied by the weighting map information of FIG. 5A, thus obtaining weighted differential phase image information. FIGS. 5B and 5C illustrate the weighted differential phase image information. FIG. 5B illustrates a weighted differential phase image in the Y direction and FIG. 5C illustrates a weighted differential phase image in the X direction. FIGS. 5B and 5C demonstrate that information associated with the region (corresponding to the substance 320) which caused phase distortion during integration in FIGS. 9B and 9C was replaced with flat information.

Figure 5D:
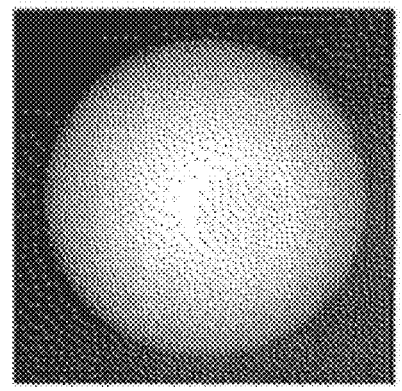
FIG. 5D illustrates a phase image simulated using the weighting map in Example 1.

The fourth obtaining unit 640 integrates the information illustrated in FIGS. 5B and 5C using the Fourier transform (S520 to S550), thus obtaining information about a phase image. FIG. 5D illustrates the phase image based on the information obtained by the fourth obtaining unit 640. Since the Fourier transform integration is the same as that described in Comparative Example, the description thereof is omitted. FIG. 5D demonstrates that not only the accuracy of information associated with the region corresponding to the low contrast region (corresponding to the substance 320) but also the accuracy of information associated with the other region were increased as compared with FIG. 9D illustrating Comparative Example.

EXAMPLE 2

Example 2 of the present invention will be described. Example 2 differs from Example 1 in the method of obtaining weighting map information. Specifically, Example 2 obtains a weighting map using a distribution of rates of absorption of X-rays by an object instead of using the distributions of moire pattern amplitudes in Example 1. In many cases, the rate of absorption by an object and the contrast of a moire pattern are correlated with each other. Accordingly, like the distributions of moire pattern amplitudes in Example 1, the distribution of X-ray absorption rates can be used as contrast information.

Figure 6:
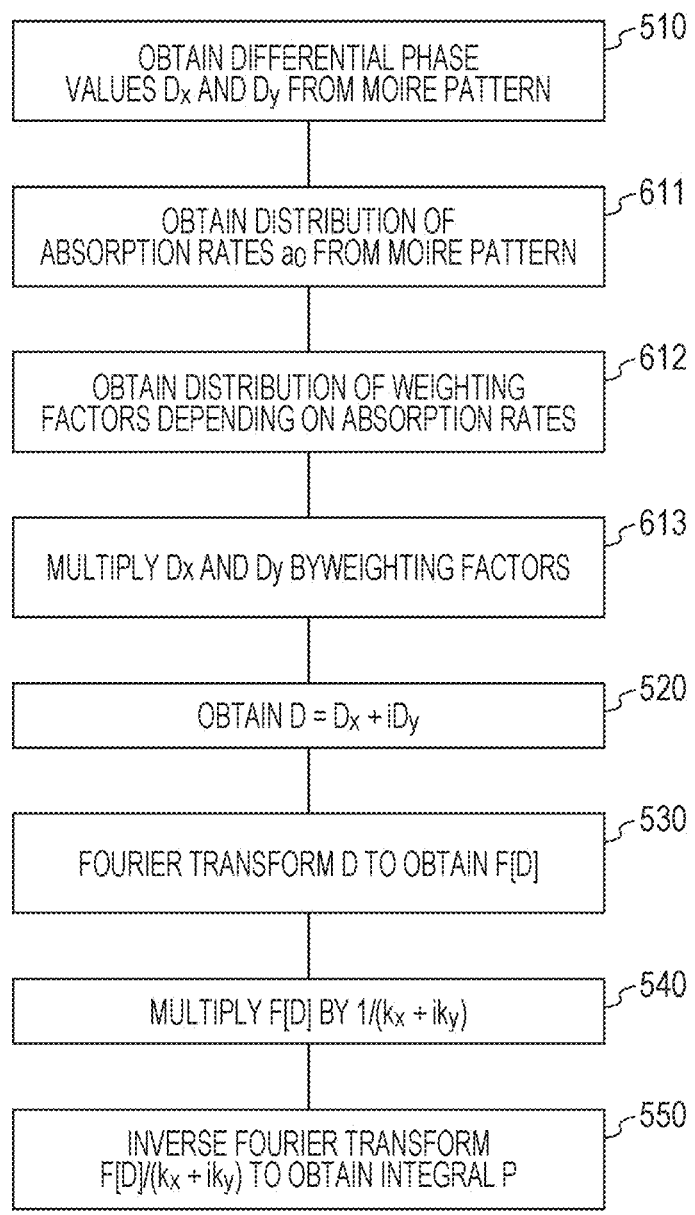
FIG. 6 is a flowchart of an arithmetic process performed by the object information obtaining apparatus in Example 2.

FIG. 6 is a flowchart of an arithmetic process performed by the object information obtaining apparatus 160 in Example 2. In Example 2, the first obtaining unit 610 obtains differential phase image information ($D_x(x, y)$ and $D_y(x, y)$) from a moire pattern (S510). The second obtaining unit 620 obtains a distribution of rates ($a_0(x, y)$) of absorption of X-rays by the object from the moire pattern (S611). The X-ray absorption rate indicates how much of incident X-rays have been absorbed. When the entire incident X-rays are absorbed, the X-ray absorption rate is 1. Then, the third obtaining unit 630 obtains information about a weighting map depending on the obtained distribution of X-ray absorption rates (S612) and multiplies the differential phase image information by the weighting map information (S613). Thus, weighted differential phase image information is obtained. The fourth obtaining unit 640 integrates the weighted differential phase image information using the Fourier transform (S520 to S550), thus obtaining information about a phase image.

Any method of obtaining the distribution of X-ray absorption rates performed by the second obtaining unit 620 may be used. Since the distribution of X-ray dosage, obtained by subtracting information relating to a moire pattern from moire pattern information, can be obtained when differential phase image information is obtained, the distribution of X-ray absorption rates may be obtained from the distribution of X-ray dosage. For example, in the Fourier transform phase demodulation, a carrier frequency peak is derived from an obtained Fourier space. A central peak (absorption peak) may be derived instead of the carrier frequency peak and the inverse Fourier transformed is performed, so that the distribution of X-ray dosage can be obtained. In Example 2, the distribution of X-ray dosage is obtained using this method and the distribution of X-ray absorption rates $a_0$ is calculated based on the distribution of X-ray dosage. In Example 2, the weighting function m is defined as follows.

[Math. 3]

$$m = \begin{cases} 1 & \text{(provided } a_0 \leq T_h) \\ a_0/T_h & \text{(provided } a_0 > T_h) \end{cases} \quad (4)$$

In Equation (4), $T_h$ denotes a given threshold. The threshold can be determined depending on various factors, e.g., an object and conditions of the apparatus. The threshold value may be constant at all times, may be changed for each imaging, or may be changed at desired time. Alternatively, the threshold value may be automatically obtained depending on various conditions by the apparatus or may be set by the user. In Example 2, $T_h=0.2$. This value is stored in the storage unit of the object information obtaining apparatus 160.

Figure 7A:
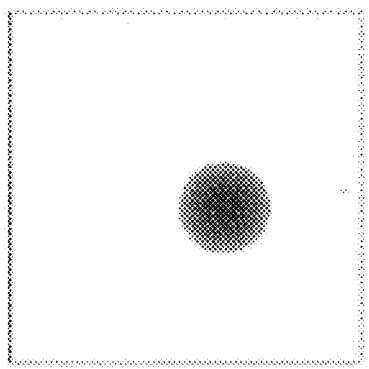
FIG. 7A illustrates a weighting map in Example 2.

The third obtaining unit 630 substitutes the X-ray absorption rates at respective coordinates obtained by the second obtaining unit 620 into the weighting function, thus obtaining information about a weighting map. In Example 2, the same moire pattern as that (see FIG. 9A) used in Comparative Example was used. FIG. 7A illustrates the weighting map obtained by the third obtaining unit 630. As the color of a region in FIG. 7A is brighter, a weighting factor for the region is closer to 1. As the color of a region is darker, a weighting factor for the region is closer to 0. FIG. 7A demonstrates that a weighting factor for the region corresponding to the low contrast region of the moire pattern is smaller than a weighting factor for the other region in the same way as the weighting map illustrated in FIG. 5A.

Figure 7B:
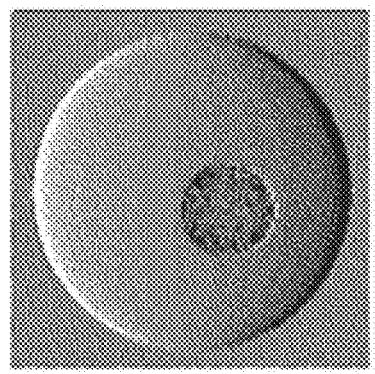
FIG. 7B illustrates a differential phase image simulated using the weighting map in Example 2.
Figure 7C:
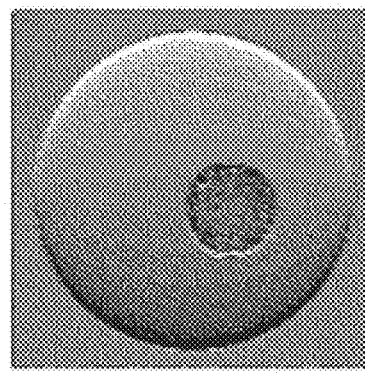
FIG. 7C illustrates another differential phase image simulated using the weighting map in Example 2.

In addition, the third obtaining unit 630 multiplies the differential phase image information, obtained by the first obtaining unit 610, by the weighting map information (S613). The differential phase image information obtained by the first obtaining unit 610 is the same obtained in Comparative Example. Images (differential phase images) based on the information are the same as those in FIGS. 9B and 9C. The differential phase image information obtained by the first obtaining unit 610 is weighted using the weighting map information illustrated in FIG. 7A, thus obtaining weighted differential phase image information. FIGS. 7B and 7C illustrate the weighted differential phase image information. FIG. 7B illustrates a weighted differential phase image in the Y direction and FIG. 7C illustrates a weighted differential phase image in the X direction in correspondence to the images in Comparative Example. FIGS. 7B and 7C demonstrate that information associated with the region (corresponding to the substance 320) which caused phase distortion during integration in FIGS. 9B and 9C was replaced with flat information.

Figure 7D:
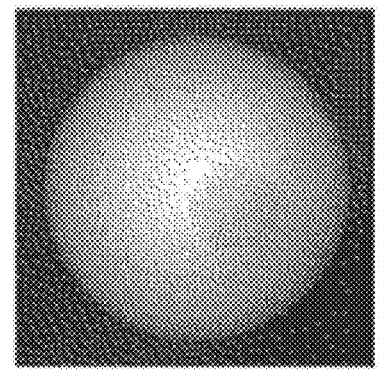
FIG. 7D illustrates a phase image simulated using the weighting map in Example 2.

The fourth obtaining unit 640 integrates the information illustrated in FIGS. 7B and 7C using the Fourier transform (S520 to S550), thus obtaining information about a phase image. FIG. 7D illustrates the phase image based on the information obtained by the fourth obtaining unit 640. Since the Fourier transform integration is the same as that described in Comparative Example and Example 1, the description thereof is omitted. FIG. 7D demonstrates that not only the accuracy of information associated with the region corresponding to the low contrast region (corresponding to the substance 320) but also the accuracy of information associated with the other region were increased as compared with FIG. 9D illustrating Comparative Example.

Quantifications in Comparative Example, Example 1, and Example 2 were compared. To compare the quantifications, Table 1 illustrates standard deviations of the differences between actual values (estimated by simulation) of the object and the phase image information obtained in Comparative Example, Example 1, and Example 2. As the standard deviation is smaller, the phase image information is closer to the actual values of the object. Table 1 demonstrates that Example 1 and Example 2 provide improved quantitative accuracy as compared to Comparative Example.

TABLE 1

|  | Standard Deviation of Errors (rad) |
| --- | --- |
| Comparative Example | 55.19 |
| Example 1 | 8.40 |
| Example 2 | 8.66 |

Example 1 and Example 2 demonstrate that weighting of differential phase image information obtained from a moire pattern using information about contrast of the moire pattern and integrating of the weighted differential phase image information are effective in improving the quantitative accuracy of a phase image.

Although weighting was performed to reduce each differential phase value associated with a region corresponding to a low contrast region in Examples 1 and 2, weighting may be performed to increase each differential phase value associated with a region corresponding to a high contrast region. In other words, it is only required that each differential phase value associated with a region corresponding to a low contrast region be relatively less than that associated with the other region after weighting.

In Examples 1 and 2, differential phase values associated with the region corresponding to the low contrast region were made smaller. This resulted in little or no phase image information associated with the region corresponding to the low contrast region in the information about the obtained phase image. Accordingly, information other than phase image information may be used to complement the region corresponding to the low contrast region, such that an image based on the resultant information may be displayed on the image display apparatus. As regards information used for complement, for example, the information (hereinafter, "X-ray dosage information") about the X-ray dosage obtained by the second obtaining unit 620 in Example 2 can be used. When the X-ray dosage information is superimposed on regions associated with small weighting factors for the differential phase image information (or regions associated with weighting factors having values other than a maximum value), the X-ray dosage information can be displayed in a region which corresponds to a low contrast region and is accordingly associated with little phase image information.

Examples 1 and 2 have been described with respect to the method of analyzing the phase of a two-dimensional moire pattern using the Fourier transform integration in the use of the X-ray Talbot interferometer as an example. The challenges that the present invention addresses, however, may be common to other cases using integration. In addition to Examples 1 and 2, the present invention can accordingly be applied to a case where, for example, imaging using a one-dimensional diffraction grating and a one-dimensional absorption grating is performed two times to obtain information about a differential phase image in the X direction and that in the Y direction individually. Furthermore, the present invention can be applied to a case where information about a differential phase image in one direction (or information about a shear image in one direction) is obtained using a one-dimensional diffraction grating and a one-dimensional absorption grating and the information is integrated to obtain information about a phase image.

[Other Embodiments]

Embodiments of the present invention can also be realized by a computer of a system or apparatus that reads out and executes computer executable instructions recorded on a storage medium (e.g., non-transitory computer-readable storage medium) to perform the functions of one or more of the above-described embodiments of the present invention, and by a method performed by the computer of the system or apparatus by, for example, reading out and executing the computer executable instructions from the storage medium to perform the functions of one or more of the above-described embodiments. The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

Furthermore, the present invention is not limited to the case where the above-described process is executed by a single processor. The process may be executed by a plurality of processors.

The present invention can provide an object information obtaining apparatus capable of, when obtaining information about a phase image from information about a differential phase image including a region where the information about the differential phase image is missing and a region where the influence of noise is large, reducing the influences of these regions, a program, and an imaging system.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-272672, filed Dec. 13, 2012, which is hereby incorporated by reference herein in its entirety.

REFERENCE SIGNS LIST

110 X-ray source
120 Object
130 Diffraction grating
140 Absorption grating
150 Detector
160 Object information obtaining apparatus
170 Image display apparatus
610 First obtaining unit
620 Second obtaining unit
630 Third obtaining unit
640 Fourth obtaining unit

The invention claimed is:

1. An object information obtaining apparatus that obtains information about a phase image of an object using information about an interference pattern produced by a shearing interferometer, the interference pattern being formed by an electromagnetic wave or electron beam passed through or reflected by the object, the apparatus comprising:
 a first obtaining unit configured to obtain information about a differential phase image of the object using the information about the interference pattern;
 a second obtaining unit configured to obtain information about contrast in each region of the interference pattern;
 a third obtaining unit configured to weight the information about the differential phase image using the information about the contrast to obtain information about a weighted differential phase image; and
 a fourth obtaining unit configured to integrate the information about the weighted differential phase image to obtain the information about the phase image of the object.

2. The apparatus according to claim 1, wherein when the second obtaining unit obtains information indicating that contrast in a second region of the interference pattern is lower than that in a first region of the interference pattern, the third obtaining unit obtains the information about the weighted differential phase image by setting a weighting factor for information which is included in the information about the differential phase image and which is associated with a region corresponding to the second region to be smaller than a weighting factor for information which is included in the information about the differential phase image and which is associated with a region corresponding to the first region.

3. The apparatus according to claim 2, wherein when the second obtaining unit obtains information indicating that contrast in a third region of the interference pattern is lower than that in the first region and is higher than that in the second region, the third obtaining unit sets a weighting factor for information which is included in the information about the differential phase image and which is associated with a region corresponding to the third region to be equal to the weighting factor for the information associated with the region corresponding to the first region or sets the weighting factor for the information associated with the region corresponding to the third region to be equal to the weighting factor for the information associated with the region corresponding to the second region.

4. The apparatus according to claim 1, wherein the third obtaining unit compares a value of information about contrast in a first region of the interference pattern to a threshold value and determines a weighing factor for information which is included in the information about the differential phase image and which is associated with a region corresponding to the first region based on a result of comparison.

5. The apparatus according to claim 4, wherein when values of the information about the contrast in all regions of the interference pattern are greater than or equal to, greater than, less than or equal to, or less than the threshold value, a constant weighting factor is used for the information about the differential phase image.

6. The apparatus according to claims 1, wherein the third obtaining unit weights the information about the differential phase image using the information about the contrast in each region and a weighting function.

7. The apparatus according to claim 6, wherein the third obtaining unit weights the information about the differential phase image using the information about the contrast in each region and the weighting function, and
wherein the weighting function is set such that at least when values of the information about the contrast in all of the regions of the interference pattern are greater than or equal to, greater than, less than or equal to, or less than a threshold value, a weighting factor is constant.

8. The apparatus according to claim 6, further comprising: a storage unit,
wherein the weighting function is stored in the storage unit.

9. The apparatus according to claim 6, wherein the weighting function is generated based on the information about the interference pattern by the third obtaining unit.

10. The apparatus according to claim 1, wherein the information about the contrast in each region of the interference pattern is information about an amplitude of the interference pattern or information about an X-ray dosage of the object in each region corresponding to that of the interference pattern.

11. The apparatus according to claim 10, wherein the information about the X-ray dosage of the object in each region corresponding to that of the interference pattern is obtained from the information about the interference pattern.

12. The apparatus according to claim 1, wherein the first obtaining unit obtains the information about the differential phase image of the object by receiving the information from a differential phase imaging device that obtains the information about the differential phase image of the object using the information about the interference pattern.

13. The apparatus according to claim 1, wherein the information about the phase image and information about an absorption image of the object are combined such that the absorption image is superimposed on a region which is included in the phase image and which corresponds to a region associated with information indicating that the contrast of the interference pattern is low, the information being obtained by the second obtaining unit.

14. An imaging system that includes a shearing interferometer and an object information obtaining apparatus configured to obtain information about a phase image of an object using information about an interference pattern produced by the shearing interferometer, the interference pattern being formed by an electromagnetic wave passed through the object, wherein the object information obtaining apparatus is the object information obtaining apparatus according to claim 1.

15. The system according to claim 14, further comprising:
an image display apparatus configured to display an image based on the information about the phase image of the object obtained by the object information obtaining apparatus.

16. The system according to claim 14, wherein the electromagnetic wave is X-rays.

17. A non-transitory storage medium storing a program that causes a computer to execute a process of obtaining information about a phase image of an object using information about an interference pattern produced by a shearing interferometer, the interference pattern being formed by an electromagnetic wave or electron beam passed through or reflected by the object, the process comprising:
obtaining information about a differential phase image of the object using the information about the interference pattern;
obtaining information about contrast in each region of the interference pattern;
weighting the information about the differential phase image using the information about the contrast to obtain information about a weighted differential phase image; and
integrating the information about the weighted differential phase image to obtain the information about the phase image of the object.

* * * * *